United States Patent
Boyd et al.

(10) Patent No.: US 11,730,934 B2
(45) Date of Patent: Aug. 22, 2023

(54) APPARATUS FOR DILATING BODILY TISSUE AND FOR MONITORING NEURAL ACTIVITY IN THE DILATED BODILY TISSUE

(71) Applicant: SPINE WAVE, INC., Shelton, CT (US)

(72) Inventors: Lawrence M. Boyd, Durham, NC (US); Mark W. Bender, Gainesville, FL (US); Matthew Penny, Holly Springs, NC (US)

(73) Assignee: SPINE WAVE, INC., Shelton, CT (US)

( * ) Notice: Subject to any disclaimer, the term of this patent is extended or adjusted under 35 U.S.C. 154(b) by 1045 days.

(21) Appl. No.: 16/420,651

(22) Filed: May 23, 2019

(65) Prior Publication Data
US 2019/0307998 A1    Oct. 10, 2019

Related U.S. Application Data

(62) Division of application No. 14/342,984, filed as application No. PCT/US2012/054051 on Sep. 7, 2012, now abandoned.
(Continued)

(51) Int. Cl.
*A61M 29/00* (2006.01)
*A61B 5/00* (2006.01)
(Continued)

(52) U.S. Cl.
CPC ............ *A61M 29/00* (2013.01); *A61B 5/296* (2021.01); *A61B 5/4893* (2013.01); *A61B 90/02* (2016.02);
(Continued)

(58) Field of Classification Search
CPC ......... A61B 2017/0262; A61B 17/025; A61M 25/007; A61M 29/00
See application file for complete search history.

(56) References Cited

U.S. PATENT DOCUMENTS 4,543,087 A * 9/1985 Sommercorn ...... A61M 5/1582
604/264
4,545,374 A    10/1985 Jacobson
(Continued)

OTHER PUBLICATIONS

International Search Report for PCT/US2012/054051, dated Jan. 7, 2013.
Writtten Opinion for PCT/US2012/054051, dated Jan. 7, 2013.

*Primary Examiner* — William R Carpenter
(74) *Attorney, Agent, or Firm* — Hoffmann & Baron, LLP

(57) ABSTRACT

An apparatus is provided herein for dilating bodily tissue and for monitoring neural activity in the distracted bodily tissue. In one aspect of the invention, the apparatus includes a first dilator having a tubular body with a distal end, a proximal end, and at least one electrode mounted about a circumference thereof; and, a second dilator having a tubular body of electrically-insulative material, the tubular body having a distal end, a proximal end, and a lumen extending therebetween sized to permit the second dilator to subsequently telescopically slide over the first dilator and come into overlapping coaxial alignment with the first dilator. A discrete window is formed through the tubular body, at or near the distal end, in communication with the lumen. With the second dilator being in overlapping coaxial alignment with the first dilator, the window is located to come into registration with at least one electrode such that, upon rotation of the second dilator relative to the first dilator, the window is positionally adjustable about the circumference of the first dilator. Advantageously, in addition to detecting the proximity of a nerve to the first dilator, the apparatus permits determination of the direction of the nerve from the first dilator. This facilitates more efficient re-positioning of the apparatus for avoidance of nerves, if a new path is necessary.

4 Claims, 16 Drawing Sheets

Related U.S. Application Data

(60) Provisional application No. 61/532,668, filed on Sep. 9, 2011.

(51) Int. Cl.
*A61B 90/00* (2016.01)
*A61B 5/296* (2021.01)
*A61M 25/00* (2006.01)
*A61M 25/01* (2006.01)

(52) U.S. Cl.
CPC ............... *A61M 2025/0008* (2013.01); *A61M 2025/0175* (2013.01); *A61M 2210/1003* (2013.01); *A61M 2230/08* (2013.01)

(56) References Cited

U.S. PATENT DOCUMENTS

| | | | |
|---|---|---|---|
| 4,769,005 A * | 9/1988 | Ginsburg | A61M 25/01 604/510 |
| 4,862,891 A | 9/1989 | Smith | |
| 4,927,418 A * | 5/1990 | Dake | A61M 25/007 604/528 |
| 5,195,541 A | 3/1993 | Obenchain | |
| 5,415,639 A * | 5/1995 | VandenEinde | A61M 25/0668 604/528 |
| 5,575,176 A | 11/1996 | Rohrs et al. | |
| 5,857,996 A | 1/1999 | Snoke | |
| 6,007,522 A * | 12/1999 | Agro | A61M 25/0169 604/533 |
| 6,099,530 A | 8/2000 | Simonian et al. | |
| 6,146,355 A | 11/2000 | Biggs | |
| 7,258,690 B2 | 8/2007 | Sutton et al. | |
| 7,273,468 B2 | 9/2007 | Bedell | |
| 7,306,574 B2 | 12/2007 | Massey et al. | |
| 8,092,415 B2 * | 1/2012 | Moehle | A61M 25/003 604/4.01 |
| 2004/0015138 A1 * | 1/2004 | Currier | A61M 25/007 604/525 |
| 2006/0036255 A1 * | 2/2006 | Pond | A61B 17/7091 606/86 R |
| 2006/0142703 A1 * | 6/2006 | Carter | A61M 25/0015 264/138 |
| 2006/0217754 A1 | 9/2006 | Boehm et al. | |
| 2007/0066977 A1 | 3/2007 | Assell et al. | |
| 2007/0191810 A1 * | 8/2007 | Kennedy | A61M 25/00 604/528 |
| 2009/0018507 A1 | 1/2009 | Schmitz et al. | |
| 2010/0145187 A1 * | 6/2010 | Weber | A61M 25/007 53/396 |
| 2011/0208226 A1 * | 8/2011 | Fatone | A61B 5/296 607/117 |

* cited by examiner

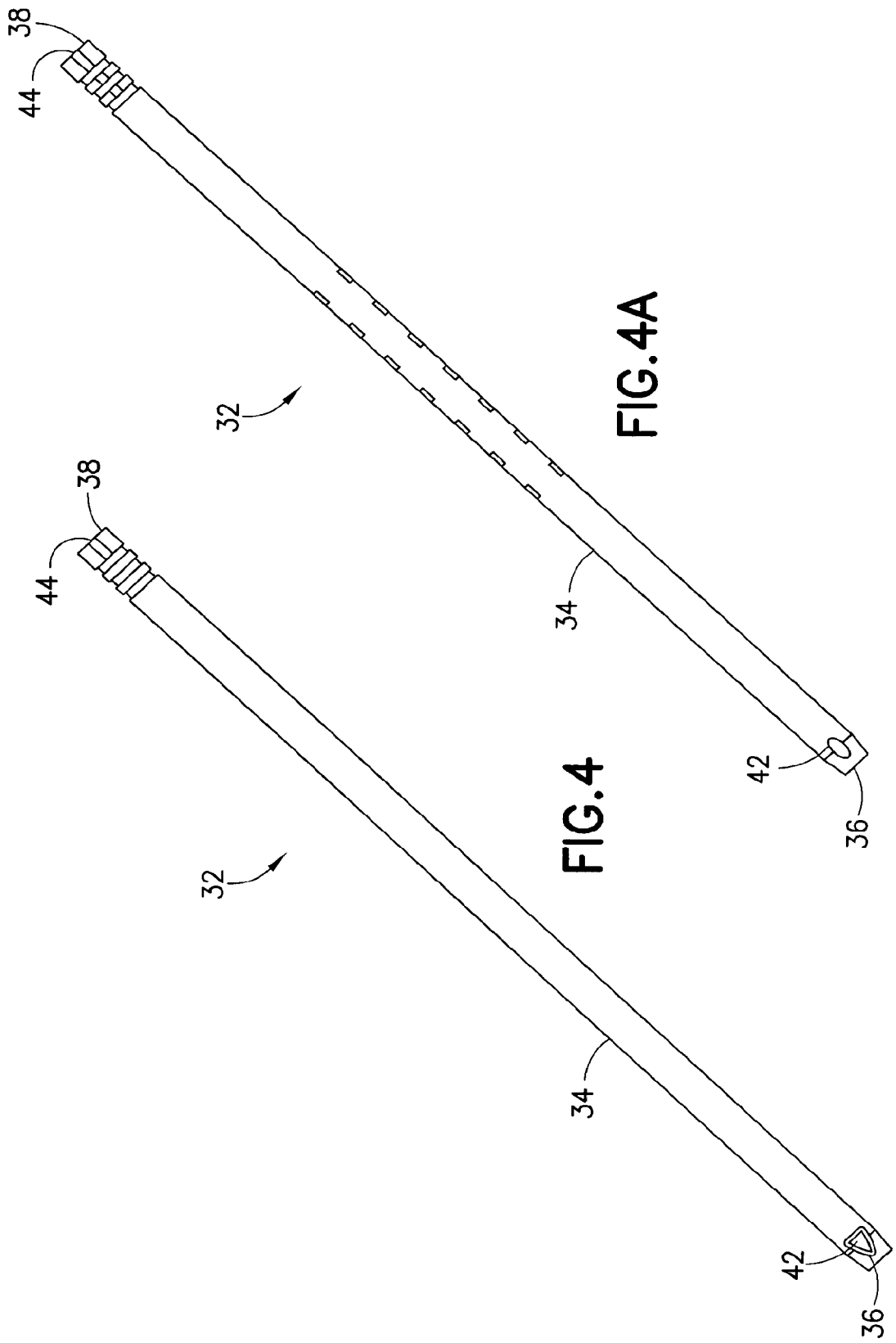

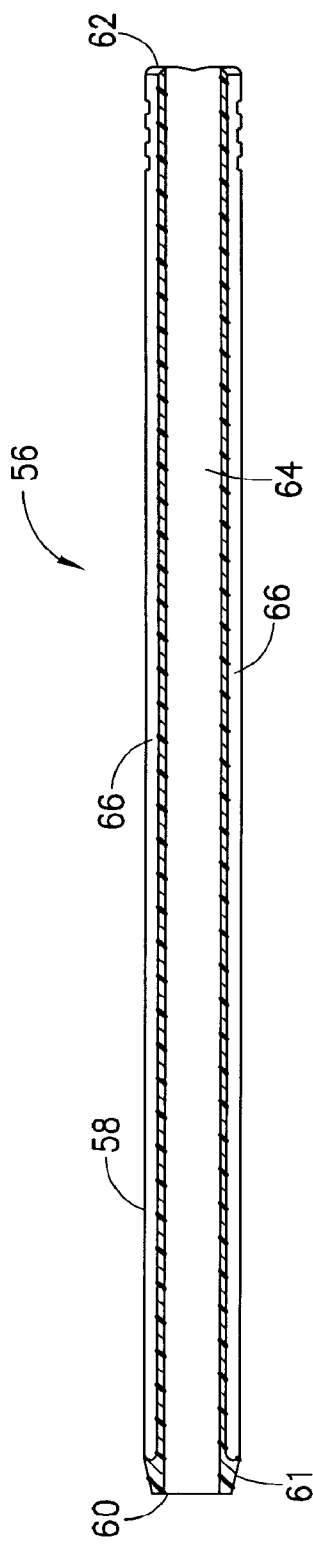
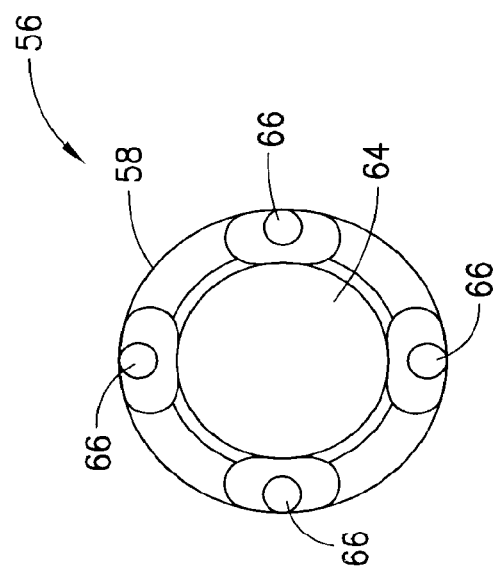

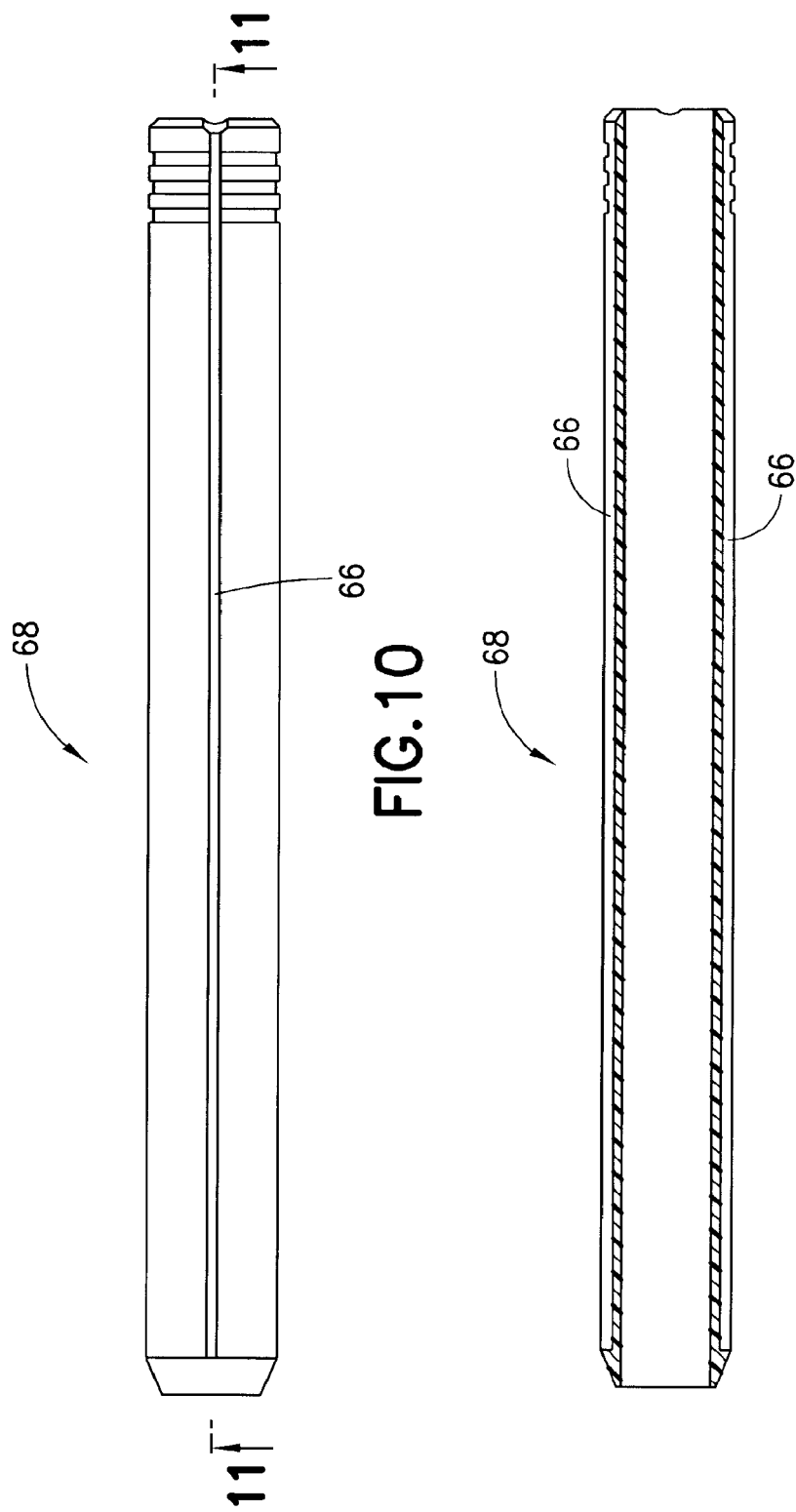

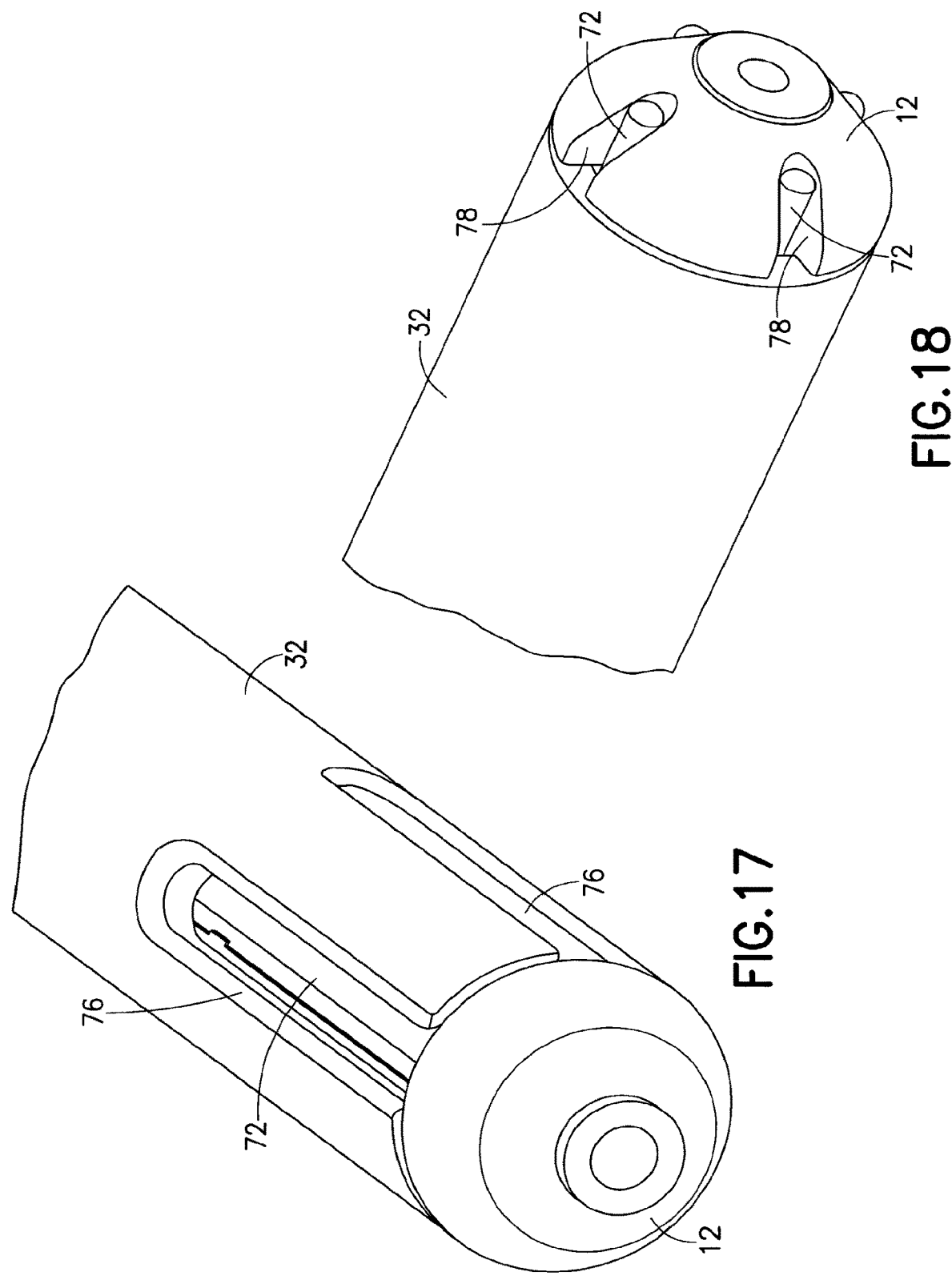

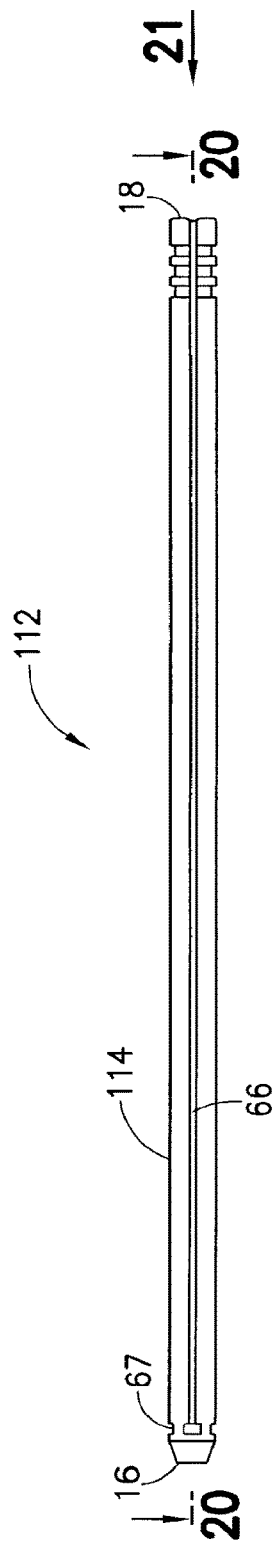
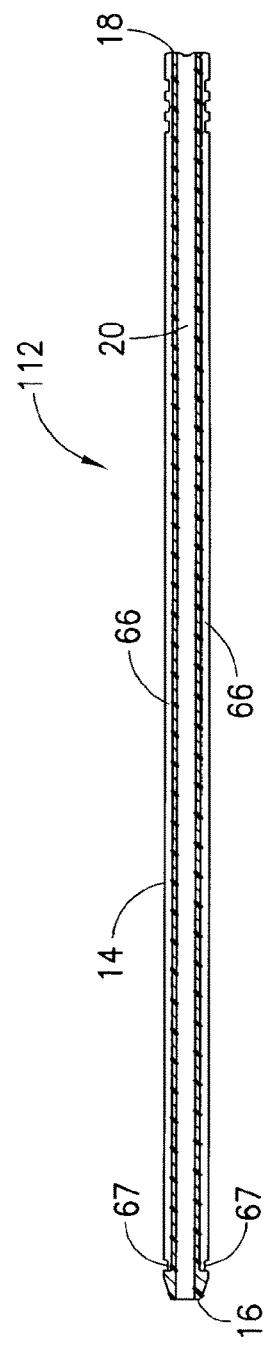
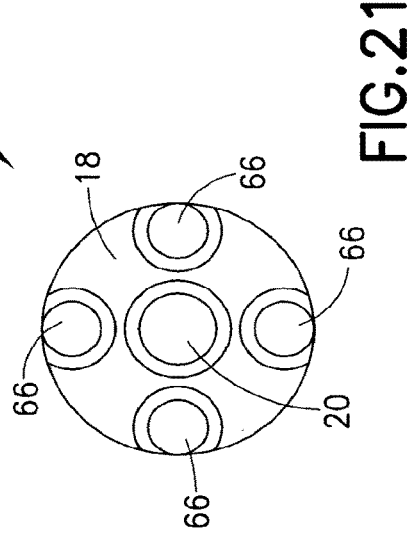

APPARATUS FOR DILATING BODILY TISSUE AND FOR MONITORING NEURAL ACTIVITY IN THE DILATED BODILY TISSUE

CROSS-REFERENCES TO RELATED APPLICATIONS

This application is a National Stage Application under 35 U.S.C. § 371 of PCT International Application No. PCT/US2012/054051, filed Sep. 7, 2012, which claims priority to Provisional Patent Application No. 61/532,668, filed Sep. 9, 2011, the entire contents of which are incorporated by reference herein.

FIELD OF THE INVENTION

The subject invention relates to apparatus and methods for dilating bodily tissue and, more particularly, for monitoring neural activity intraoperatively in bodily tissue being dilated.

BACKGROUND OF THE INVENTION

Surgery requires the introduction of various instruments into the body. Direct, or even close, engagement with nerves by surgical instruments may result in nerve damage potentially leaving a lasting deleterious effect on a patient. This concern becomes greater where larger instruments must be introduced thus increasing the potential for harmful engagement with a nerve.

Lateral access to the spine, in a direction transverse to the anterior-posterior axis, may be desired for certain procedures, for example, for vertebral interbody fusion. Lateral access, however, requires passage through a psoas muscle which is located on both sides of the spine. Increased nerve density within the psoas muscle adds difficulty to the lateral access technique. To avoid nerve contact, electromyography (EMG) techniques have been utilized which intraoperatively monitor electrical activity to evaluate nerve location. A basic EMG technique for intraoperative neuromonitoring utilizes a monopolar probe which includes an electrified tip that is insertable into bodily tissue. Current is applied to the tip with a ground electrode attached to the skin. Current is introduced through the probe and the activity of surrounding nerves is monitored using electrodes placed on muscles innervated by the nearby nerves (knows as myotomes). Activation of a muscle action potential by the electrical stimulus threshold value indicates proximity to a nerve. Such threshold levels are known in the art. Upon detection of a nerve, the probe is re-located with the process repeated to further evaluate proximity of nerves. The intended goal is to locate a passage through the bodily tissue at sufficient distance from surrounding nerves. The described prior art technique provides a finding of how close a nerve is located to the probe (determined by the current reading). Other known art describes the specific location or direction of the detected nerve relative to the probe. However, improvements in determining nerve location as well as direction, particularly in lateral access spinal surgery is desired.

SUMMARY OF THE INVENTION

An apparatus is provided herein for dilating bodily tissue and for monitoring neural activity in the dilated bodily tissue. In one aspect of the invention, the apparatus includes a first dilator having a tubular body with a distal end, a proximal end, and at least one electrode mounted about a circumference thereof; and, a second dilator having a tubular body of electrically-insulative material, the tubular body having a distal end, a proximal end, and a lumen extending therebetween sized to permit the second dilator to subsequently telescopically slide over the first dilator and come into overlapping coaxial alignment with the first dilator. A discrete window is formed through the tubular body, at or near the distal end, in communication with the lumen. With the second dilator being in overlapping coaxial alignment with the first dilator, the window is located to come into registration with at least one electrode such that, upon rotation of the second dilator relative to the first dilator, the window is positionally adjustable about the circumference of the first dilator. Advantageously, with the subject invention, in addition to detecting the proximity of a nerve to the first dilator, the apparatus permits determination of the direction of the nerve from the first dilator. This facilitates more efficient re-positioning of the apparatus for avoidance of nerves, if a new path is necessary.

In a further aspect of the subject invention, a plurality of electrodes, spaced about the circumference of the first dilator, may be used in place of the annular electrode. The electrodes are independently electrified and monitored so as to permit evaluation of each electrode relative to possible proximate nerves.

In yet a further aspect of the subject invention, an electrode may be sequentially introduced about the circumference of the first dilator to evaluate proximity of nerves.

As used herein, the term "distal", and derivatives thereof, shall refer to a direction towards a patient, while the terminal "proximal", and derivatives thereof, shall refer to a direction away from a patient and towards the operating surgeon.

These and other aspects of the invention will be better understood through a study of the following detailed description and accompanying drawings.

BRIEF DESCRIPTION OF DRAWINGS

FIGS. 3, 3A, 4 and 4A depict a second dilator formed in accordance with the subject invention;

FIG. 9 is a cross-sectional view taken along line 9-9 of FIG. 8;

FIG. 9A is an end view as seen along line 9A-9A of FIG. 8;

FIG. 10 is a top plan view of a fourth dilator formed in accordance with the subject invention;

FIG. 11 is a cross-sectional view taken along line 11-11 of FIG. 10;

FIGS. 17 and 18 show a variation of the subject invention using a plurality of electrodes with corresponding windows being formed in the second dilator; and, FIGS. 19-21 show a variation of the first dilator including a plurality of channels with FIG. 20 being a cross-sectional view taken along line 20-20 of FIG. 19 and FIG. 21 being an end view taken along line 21-21 of FIG. 19.

DETAILED DESCRIPTION OF THE INVENTION

With reference to the Figures, various apparatuses and techniques for dilating bodily tissue and for monitoring neural activity in the dilated bodily tissue are shown. The apparatuses are described herein for use with spinal lateral access surgery. As will be appreciated by those skilled in the art, the apparatuses may be utilized in other surgical applications, such as posterior or posterior-lateral access spinal surgery, as well as, in surgical applications in other parts of the body. The apparatuses provide for the preparation of a working access channel to a target site by sequentially dilating bodily tissue while permitting intraoperative neural monitoring to evaluate proximity of the inserted apparatus to surrounding nerves.

Figure 1:
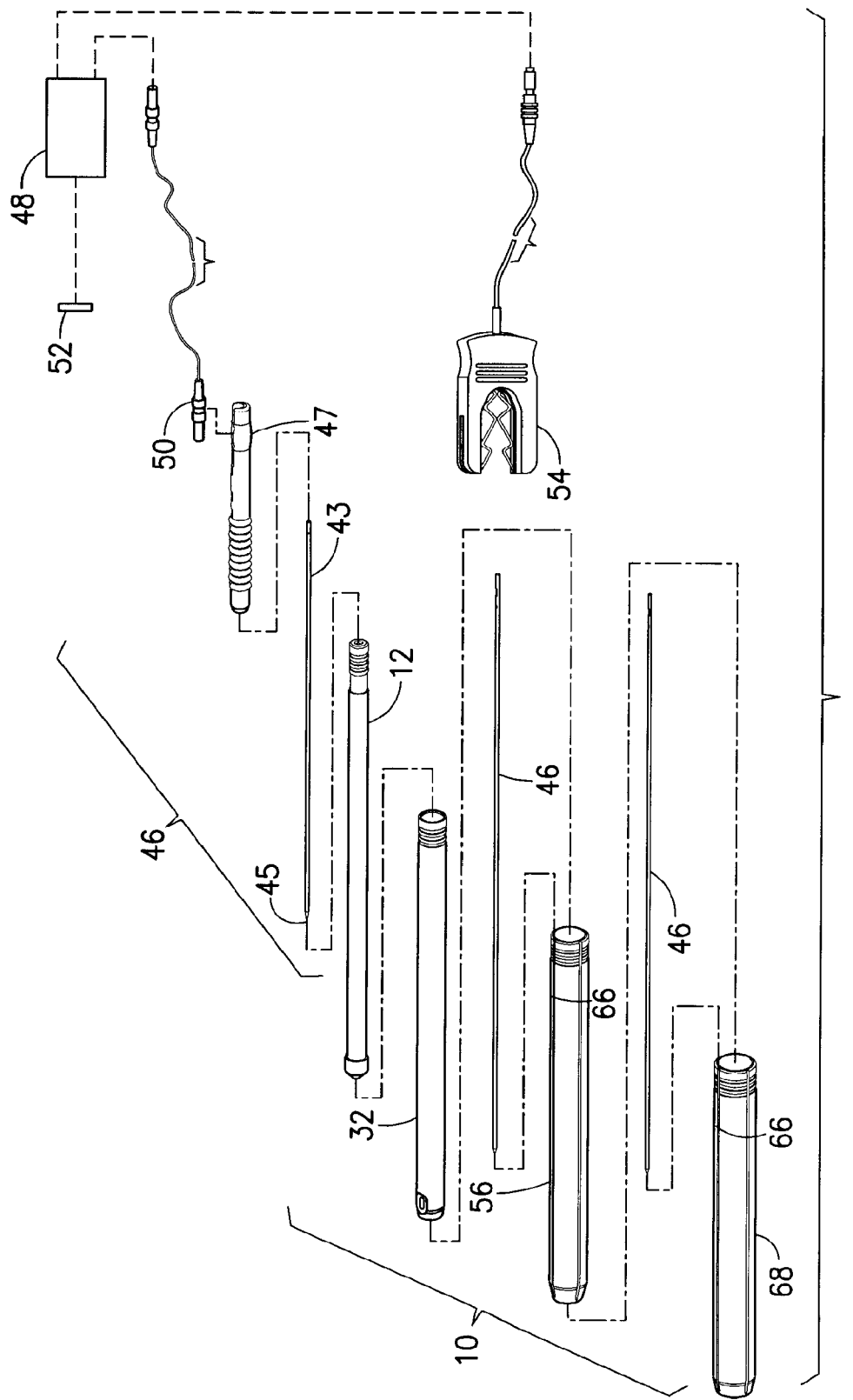
FIG. 1 is an exploded view of an apparatus formed in accordance with the subject invention.
Figure 2:
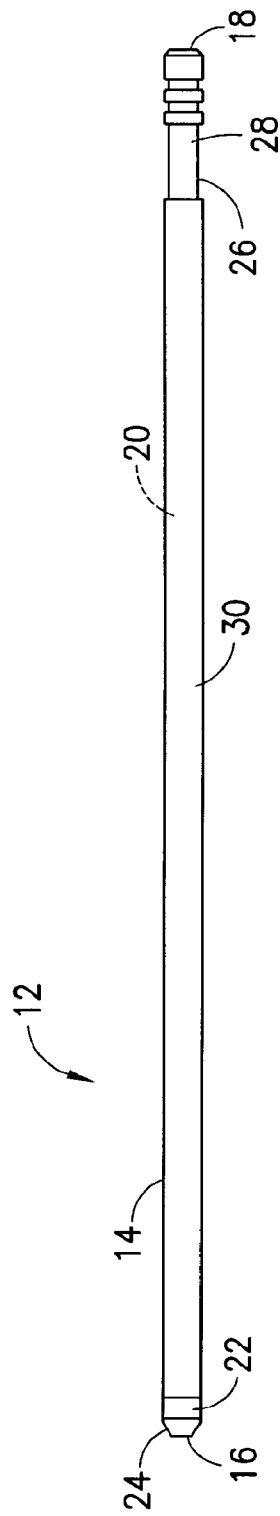
FIG. 2 is a top plan view of a first dilator formed in accordance with the subject invention.

In a first embodiment, an apparatus 10 is provided which, as shown in FIGS. 1 and 2, generally includes a first dilator 12 having a tubular body 14 with a distal end 16, a proximal end 18 and a lumen 20 extending therebetween. The lumen 20 is sized to permit passage therethrough of the shaft of a monopolar probe or a guide wire, as described below.

An annular electrode 22 is mounted about a circumference of the tubular body 14, preferably in a position closer to the distal end 16 than the proximal end 18. The tubular body 14 preferably includes a rounded or tapered portion 24 at the distal end 16 surrounding the lumen 20 which acts as a wedge to allow for a gradual dilation of bodily tissue as the first dilator 12 advances into the bodily tissue. The electrode 22 may be located on or proximally of the portion 24. To permit electrical flow from the electrode 22 in a controlled manner, portions of the tubular body 14 adjacent to the electrode 22 may be formed with electrically-insulative material. A conductor 26 may extend through the tubular body 14 which is electrically coupled to the electrode 22 and includes an exposed portion 28 preferably located in proximity to the proximal end 18. A layer of electrically-insulative material 30 is provided on the conductor 26 to separate the electrode 22 from the exposed portion 28. With this configuration, current applied to the exposed portion 28 may be conducted through the conductor 26 and to the electrode 22 as needed.

The first dilator 12 is preferably provided with a length of at least 25.4 cm between the distal and proximal ends 16, 18 so as to have sufficient length to extend from a target site inside of the body with the proximal end 18 being exposed outside of the body. Also, the first dilator 12 preferably has an outside diameter of about 6 mm.

Figure 3:
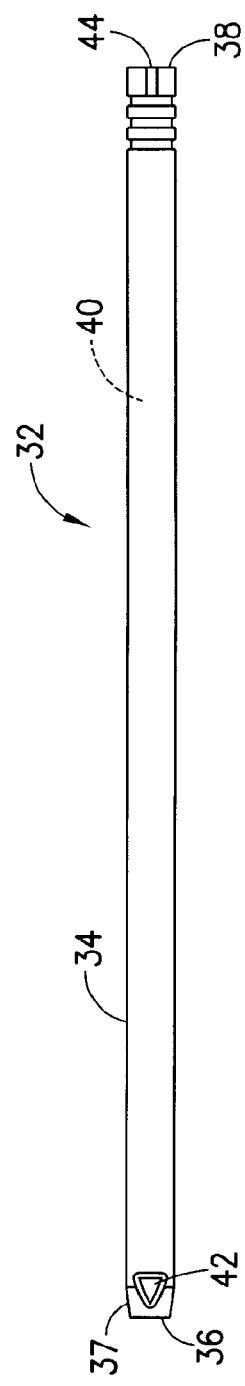

In the first embodiment, the apparatus 10 also includes a second dilator 32 which, as shown in FIGS. 3 and 4, includes a tubular body 34 having a distal end 36, a proximal end 38 and a lumen 40 extending therebetween. A rounded or tapered portion 37 is provided at the distal end 36 for easing dilation of bodily tissue with advancement of the second dilator 32 into the bodily tissue. The lumen 40 is sized to permit the second dilator 32 to telescopically slide over the first dilator 12 and come into overlapping coaxial alignment with the first dilator 12. To facilitate this arrangement, it is preferred that the diameter of the lumen 40 be formed slightly larger than the outer diameter of the first dilator 12. It is also preferred that the second dilator 32 have a shorter length than the first dilator 12 with a length of about 23 cm being provided between the distal and proximal ends 36, 38. In this manner, with the distal end 36 of the second dilator 32 being generally aligned with the distal end 16 of the first dilator 12, the first dilator 12 will extend proximally beyond the second dilator 32. The second dilator 32 preferably has an outer diameter of about 8 mm.

A discrete window 42 is formed through the tubular body 34 in communication with the lumen 40. The window 42 is located so as to come into registration with the electrode 22 with the second dilator 32 being in overlapping coaxial alignment with the first dilator 12. With this arrangement, upon rotation of the second dilator 32 relative to the first dilator 12, the window 42 is positionally adjustable about the circumference of the first dilator 12 and about the electrode 22. This allows for current flowing out of the electrode 22 to be focused in a particular radial direction into the surrounding tissues. The second dilator 32 is provided with a mark or other suitable indicia 44 at or adjacent to the proximal end 38 which is axially aligned with the window 42. In this manner, with the window 42 being located inside of a patient and not being directly visually observable, the mark 44 provides for a visual indication of the angular position of the window 42 about a central axis of the second dilator 32.

Figure 3A:
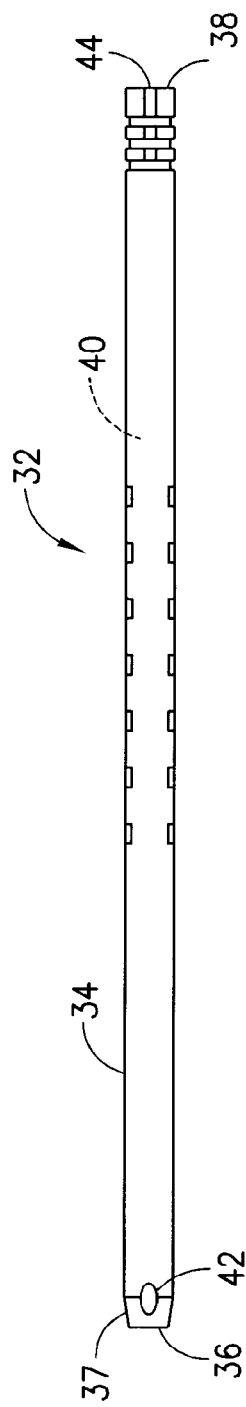

The window 42 may be formed with various configurations. As shown in FIGS. 3 and 4, the window 42 may be polygonal (e.g., triangular). Intersecting corners may be rounded or otherwise formed to avoid sharp angular transitions between sides of the polygon. Alternatively, as shown in FIGS. 3A and 4A, the window 42 may be elliptical having a circular or oval shape.

The apparatus 10, utilizing the first and second dilators 12, 32, may be used as follows. In one procedure, a monopolar probe 46 is initially provided which includes a shaft 43 that terminates in a sharpened tip 45, and a handle 47 mounted to the shaft 43. The monopolar probe 46 is configured to be releasably attached to a source of electricity 48 such as by a jack 50. A ground or reference electrode 52 is attached to the patient's skin and also electrically coupled to the source of electricity 48 such that with the monopolar probe 46 being inserted into a patient, a closed electrical circuit is defined between the monopolar probe 46 and the ground electrode 52. Additional surface or needle electrodes are placed on the muscle groups (myotomes) that are innervated by the nerve roots around the particular spinal segments where the surgeon is performing tissue dilation. It is preferred that the source of electrical current 48 be provided with controls for controlling the level of electrical output and measuring apparatus for monitoring the level of the electrical output from the electrodes on the various myotomes, particularly the magnitude of current output.

Figure 5A:
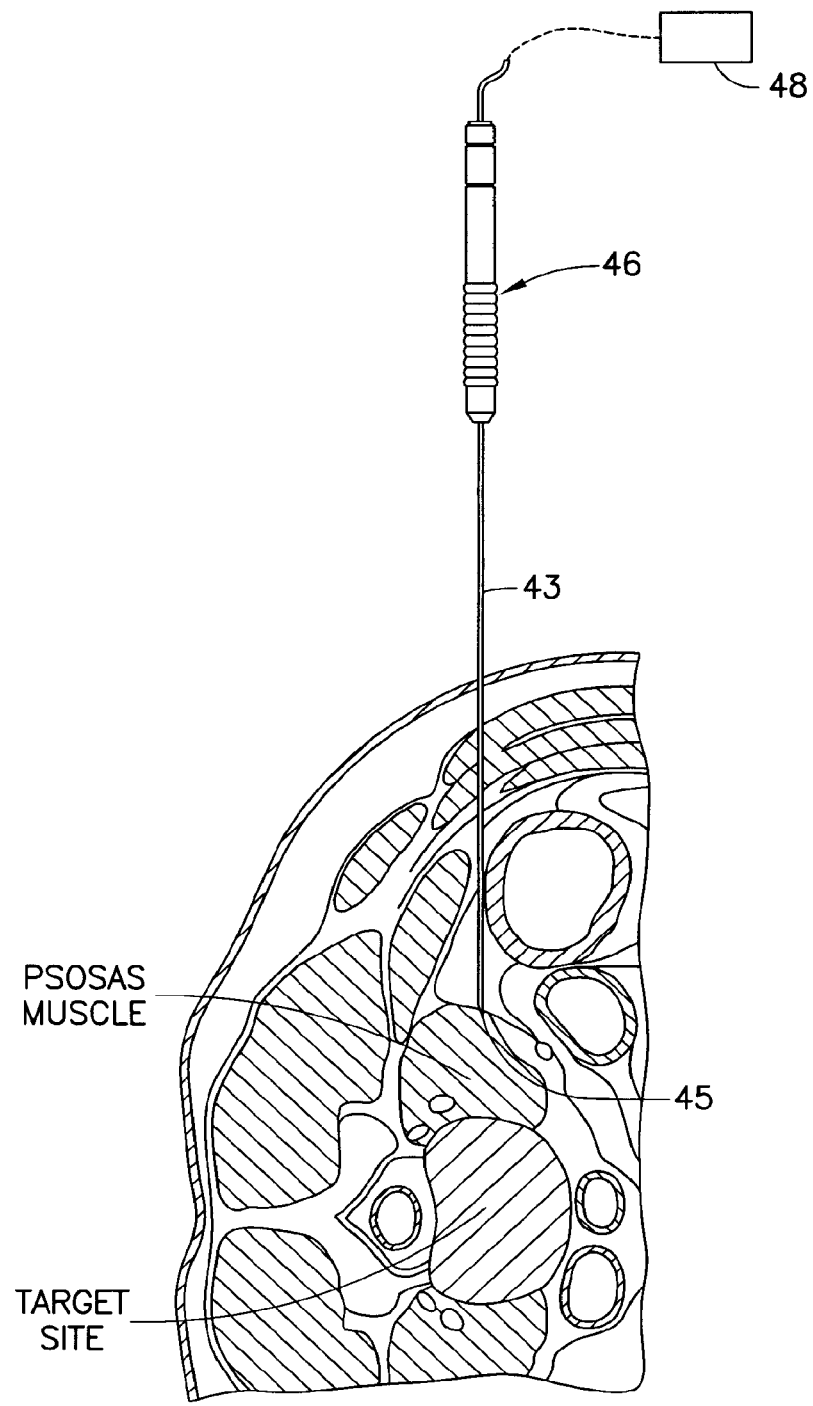
FIGS. 5a-5c show the process of a monopolar probe being inserted into a target site in accordance with the subject invention.
Figure 5B:
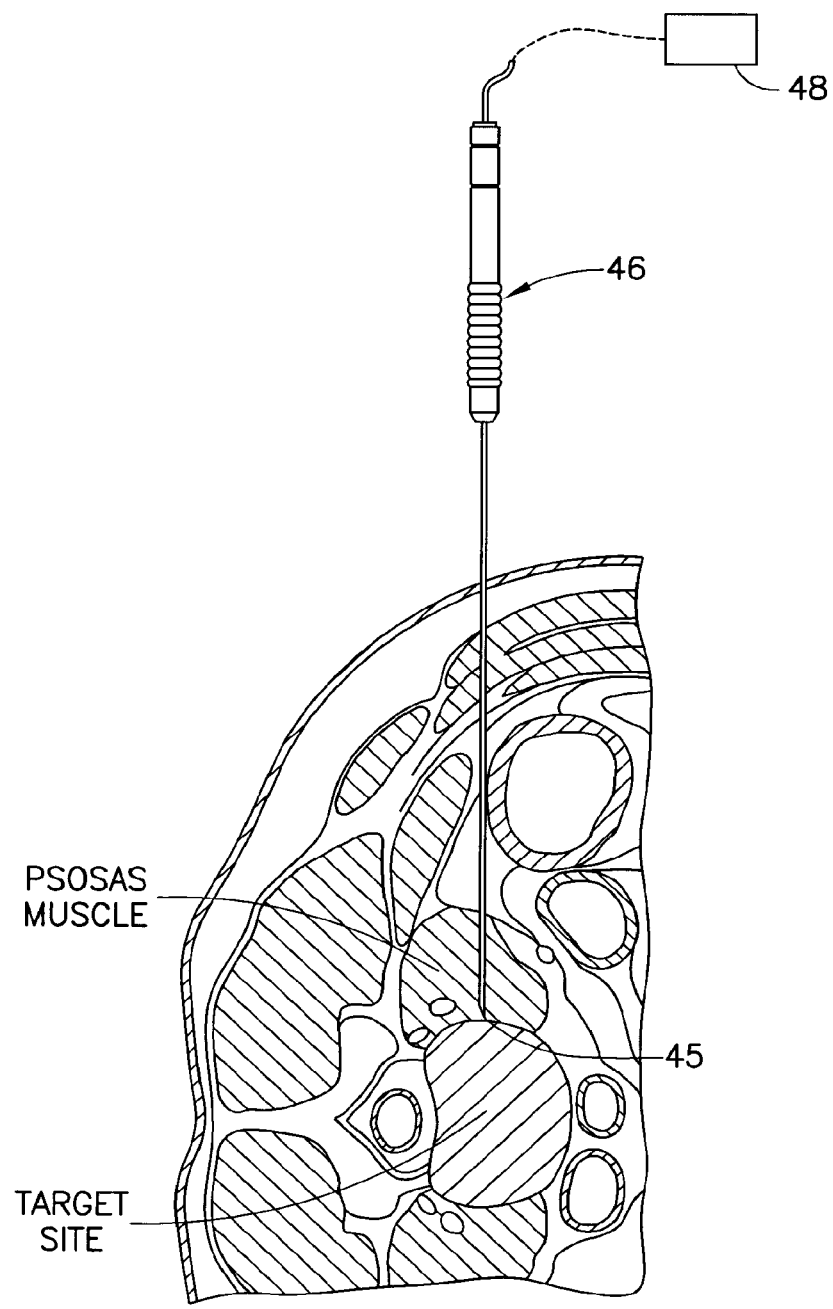
Figure 5C:
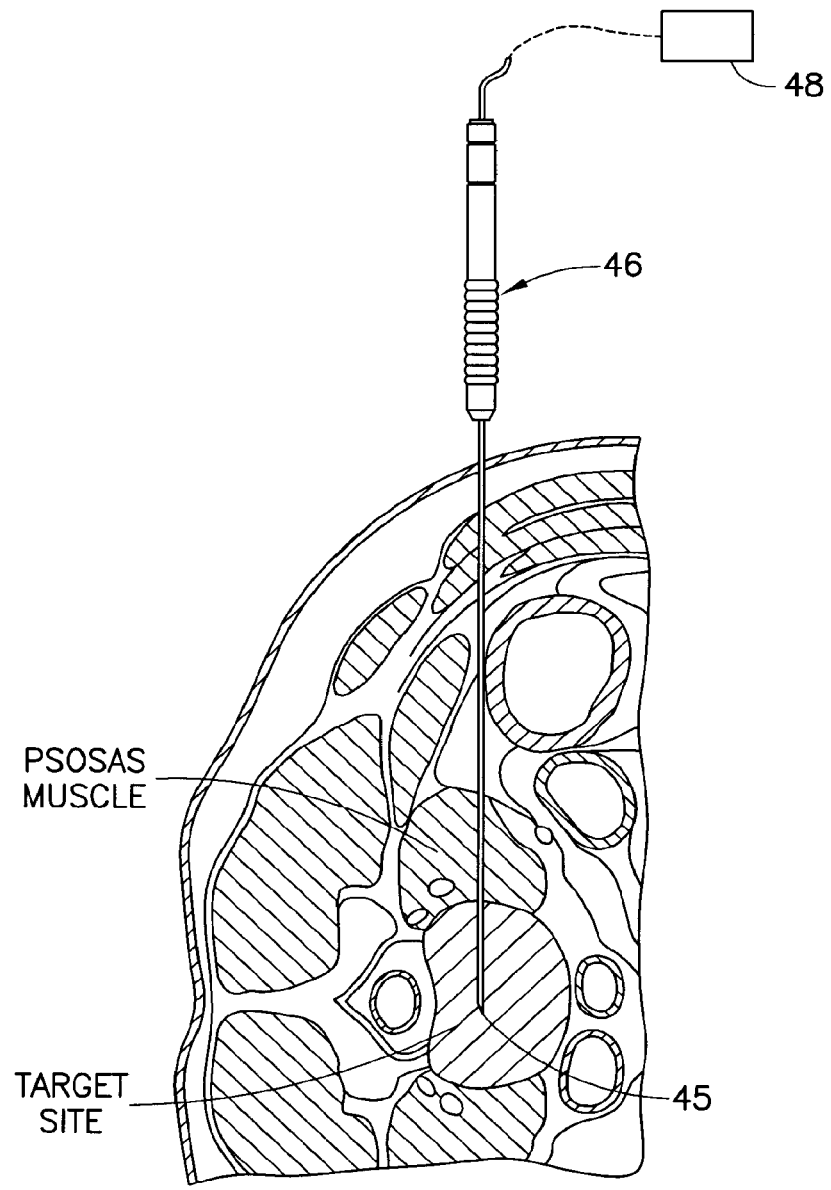

Once initial preparations have been made, the tip 45 of the monopolar probe 46 is caused to be inserted into a patient and directed towards a target site (FIG. 5a). Fluoroscopy or other radiological techniques may be used to guide the monopolar probe 46 to the target site. With lateral access spinal surgery, the monopolar probe 46 is introduced in a lateral direction relative to the spine, which is perpendicular to the anterior-posterior axis as described in U.S. Pat. No. 4,545,374 issued to Robert E. Jacobson on Oct. 8, 1985 and entitled "Method and Instruments for Performing a Percutaneous Diskectomy" incorporated herein by reference in its entirety. The tip 45 may be introduced into the body until close or touching engagement with the psosas muscle (FIG. 5*a*). Using the known technique of "mapping", the tip 45 of the monopolar probe 46 may be electrified with the tip 45 being positionally adjusted about the surface of the psosas muscle to evaluate electrical activity prior to insertion thereinto. Those skilled in the art will recognize proximate neural presence based on variations in the detected level of current. Where an acceptable site is located, the monopolar probe 46 is advanced so as to pierce into the psosas muscle (FIG. 5*b*) and into the target site (FIG. 5*c*). Electrical levels in the muscle electrodes may be monitored during the advancement of the monopolar probe 46. If neural presence is detected, the monopolar probe 46 may be re-located. The advancement of the tip 45 into the target site provides anchoring of the shaft 43 to the target site. Once secured, the source of electricity 48 may be decoupled from the monopolar probe 46, the handle 47 may be removed with the shaft 43 of the monopolar probe 46 acting as a guide wire to the target site.

Thereafter, the first dilator 12 is caused to telescopically slide over the monopolar probe 46 with the shaft 43 passing into the lumen 20. Preferably, the first dilator 12 is twisted or rotated as it is being advanced in order to facilitate tissue dissection. With the first dilator 12 having a greater outer diameter than the shaft 43, tissue surrounding the apparatus 10 is caused to dilate upon advancement of the first dilator 12 into the body. The source of electricity 48 may be coupled to the first dilator 12, particularly at the exposed portion 28, during advancement of the first dilator 12 along the shaft 43. This permits for intraoperative neural monitoring globally about the shaft as the first dilator 12 is advanced. The first dilator 12 is introduced with the distal end 16 coming into proximity with the target site.

Figure 1A:
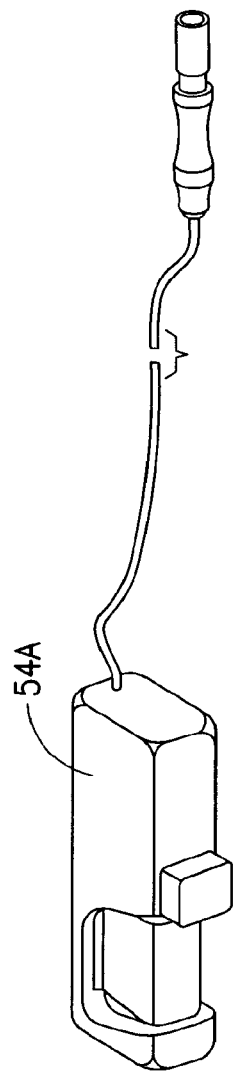
FIG. 1A shows an alternative clip useable with the subject invention.
Figure 6:
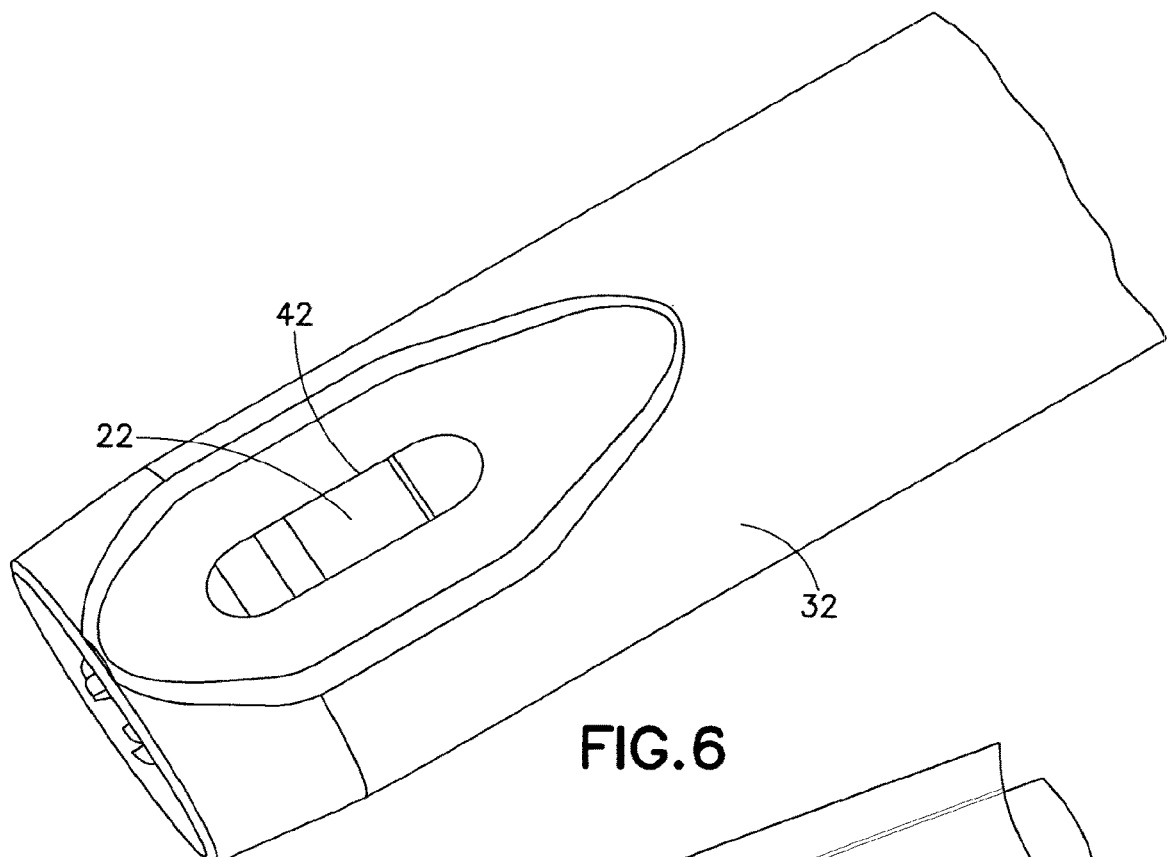
FIGS. 6 and 7 depict the first and second dilators being assembled together for use.
Figure 7:
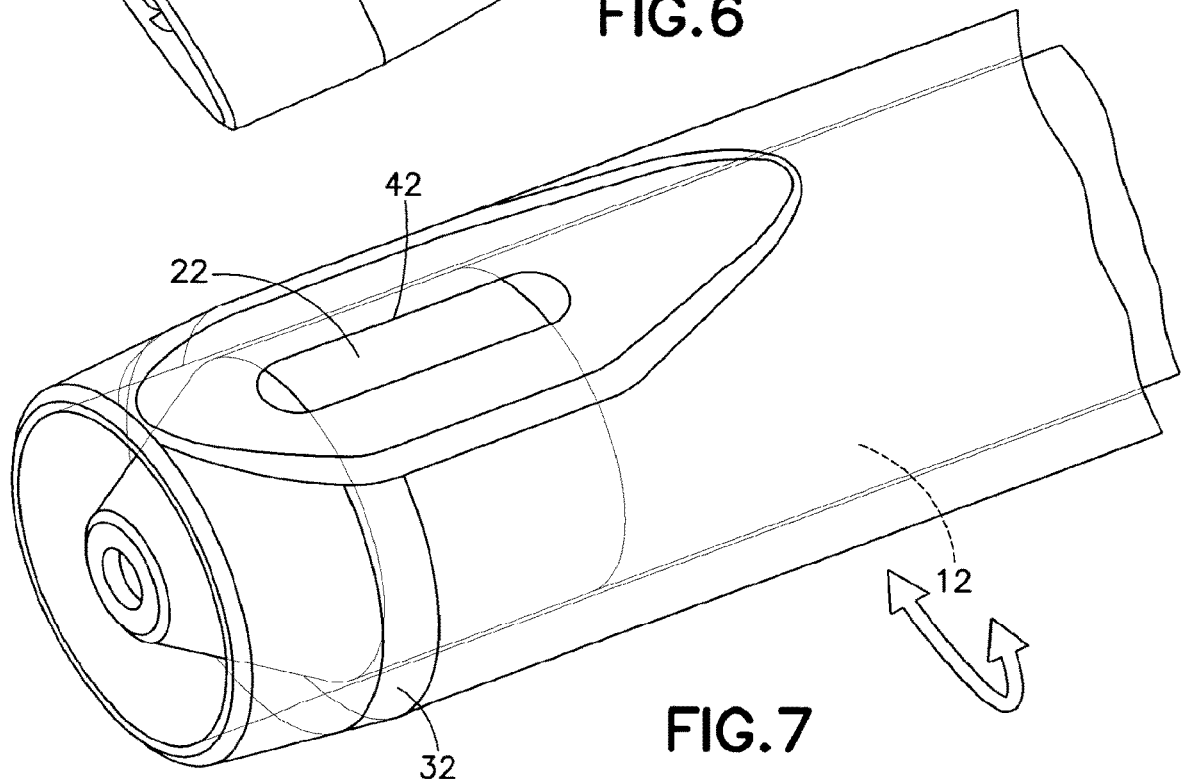

Thereafter, the second dilator 32 may be telescopically slid over the first dilator 12 with advancement of the second dilator 32 into the body causing further dilation of surrounding bodily tissue. The second dilator 32 is advanced with the distal end 36 coming generally into alignment with the distal end 16, as shown in FIG. 6. In this position, the window 42 is in axial registration with the electrode 22. The source of electricity 48 is coupled to the exposed portion 28 of the first dilator 12 such as with a clip 54, 54A. As shown in FIG. 1, the clip 54 may be formed to resiliently engage the first dilator 12 (e.g., having a spring clip element), or, the clip 54A, as shown in FIG. 1A, may be manually adjustable (e.g., a slide lock) to engage the first dilator 12. The second dilator 32 is then caused to rotate about the first dilator 12 with the window 42 being positionally adjusted about the electrode 22 (FIG. 7). This allows for a focused flow of current to be controllably released from the electrode 22 about the circumference of the apparatus 10. During a course of the rotation of the second dilator 32 relative to the first dilator 12, the level of electrical activity in the muscle electrodes is monitored. If a sufficiently significant change in electrical activity (a compound muscle action potential) is detected which indicates the presence of a proximate nerve, the approximate distance of the nerve from the apparatus 10 may be estimated by the current magnitude of stimulation current and the direction of the detected nerve from the apparatus 10 may be visually observed by the position of the mark 44 corresponding to the location of the observed change in electrical flow. With this information, the surgeon may retract the apparatus 10 and re-position the monopolar probe 46 in a direction away from the detected nerve at a distance of at least that estimated by the observed electrical change. The procedure may be repeated with the introduction in sequence of the monopolar probe 46, the first dilator 12 and the second dilator 32, as described above, to evaluate the proximity of any nerves relative to the re-positioned assembly. If no proximate nerves are detected, the procedure may continue. If, however, a proximate nerve is detected, the process may be repeated until an acceptable passage is detected.

Figure 8:
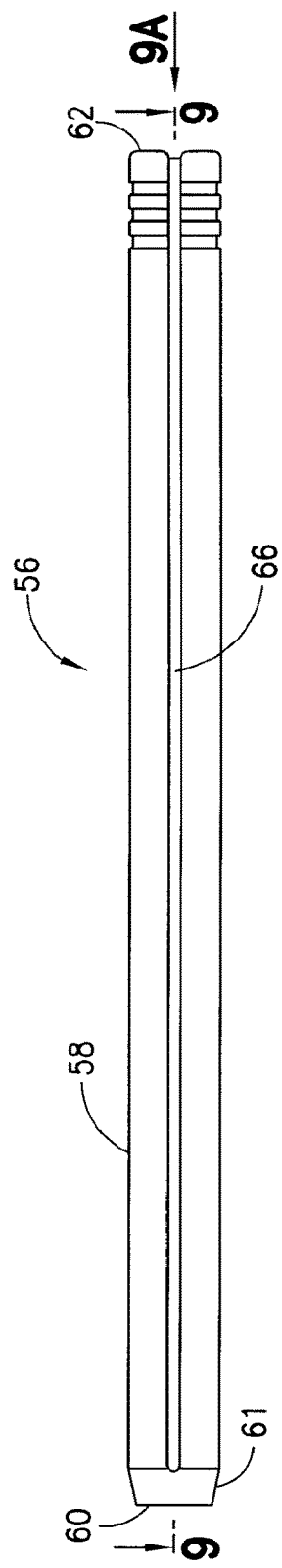
FIG. 8 is a top plan view of a third dilator formed in accordance with the subject invention.

To allow for additional dilation of the surrounding bodily tissue, a third dilator 56, as shown in FIGS. 8 and 9, may be provided having a tubular body 58 with a distal end 60, a proximal end 62 and a lumen 64 extending therebetween. A rounded or tapered portion 61 may be provided at the distal end 60 for easing dilation of bodily tissue with advancement of the third dilator 56 into the bodily tissue. The lumen 64 is sized to permit the third dilator 56 to telescopically slide over and come into coaxial alignment with the second dilator 32. The larger outer diameter of the third dilator 56, as compared to the outer diameter of the second dilator 32, provides for additional dilation of surrounding bodily tissue. The third dilator 56 may be formed with a length of about 21 cm and an outer diameter of about 12.5 mm. The third dilator 56 is preferably shorter than the first and second dilators 12, 32 to allow for access thereto while in a telescoped relationship.

It may be desired to intraoperatively monitor for neural activity about the third dilator 56. The third dilator 56 is formed of electrically-insulative material which does not permit the passage therethrough of current which would emanate from the electrode 22. To permit neural monitoring about the third dilator 56, a plurality of axially extending channels 66 may be formed about the circumference of the tubular body 58, preferably at four substantially equally spaced locations (FIG. 9A). It is preferred that the channels 66 be generally straight and be located to be accessible from towards the proximal end 62 with the third dilator 56 being located inside of a patient. The channels 66 may extend from the proximal end 62. In use, as shown schematically in FIG. 1, a monopolar probe 46 may be sequentially inserted into each of the channels 66 with an electrical monitoring being conducted about the distal end 60 at each site. With this arrangement, proximity to any surrounding nerves may be evaluated, as well as the direction towards such nerves. The spacing of the channels 66 allows for evaluation of sectors or quadrants about the third dilator 56 to obtain a general direction towards a detected nerve.

Figure 8A:
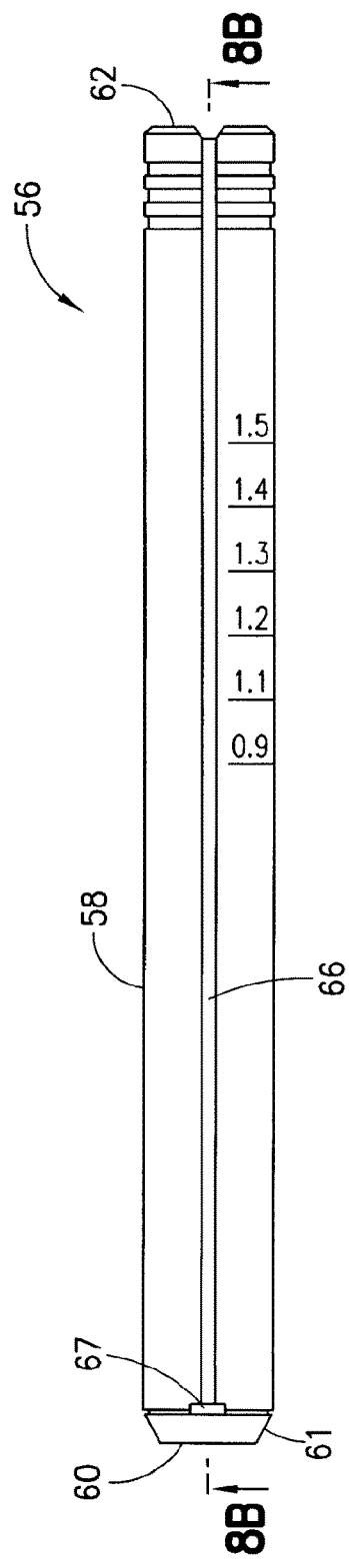
FIG. 8A is a top plan view of an alternative third dilator formed in accordance with the subject invention.
Figure 8B:
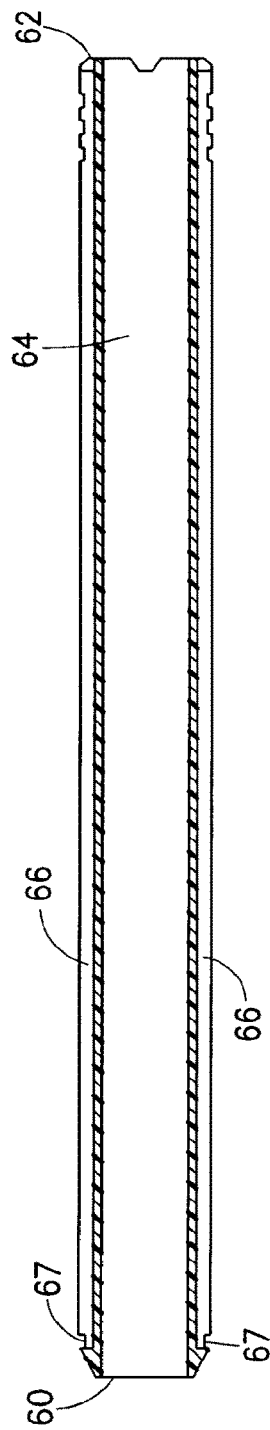
FIG. 8B is a cross-sectional view taken along line 8B-8B of FIG. 8A.

As shown in FIGS. 8 and 8A, the channels 66 may be formed to terminate spaced from the distal end 60 of the tubular body 58. In addition, as shown in FIGS. 8A and 8B, at the distal terminus of one or more of the channels 66, a transverse channel 67 may be provided which is disposed transversely to, and is in communication with, the respective channel 66. The transverse channel 67 provides a radial expanse extending from the distal terminus of the channel 66 which may provide for enhanced signal transmission from a monopolar probe 46 disposed in the respective channel 66. The transverse channel 67 may be of limited radial extent about the circumference of the tubular body 58 so as to not circumscribe the tubular body 58. Optionally, one or more of the transverse channels 67 may be extended to overlap two or more of the channels 66, including having one transverse channel 67 circumscribe the circumference of the tubular body 58 in being in communication with all of the channels 66.

Additional dilators, such as fourth dilator 68 may then be provided and formed in similar manner to the third dilator 56 but at increasing diameters so as to provide for telescoping engagement about the assembly 10 with ever-increasing dilation of surrounding bodily tissue. Each dilator of greater diameter is also provided with shorter length to permit access to components located therewithin, yet the dilators must be provided with sufficient length to extend from the body during use. The channels 66 may be provided in each of the fourth dilator 68 and any additional outer dilators to permit neural monitoring in the same manner as described with respect to the third dilator 56. The fourth dilator 68 may also be formed to have expanded windows 67 similar to third dilator 56 as described with respect to FIGS. 8 and 8A.

In an alternate procedure, a surgeon may choose to insert the first dilator 12 without the use of the monopolar probe 46. With this procedure, the first dilator 12 is inserted with the distal end 16 being located adjacent to the target site. Fluoroscopy or other radiological techniques may be used to guide the first dilator 12 to the target site. The source of electricity 48 may be coupled to the first dilator 12, particularly at the exposed portion 28, during advancement of the first dilator 12 into the bodily tissue. This permits for intraoperative neural monitoring as the first dilator 12 is advanced. Thereafter, to secure the first dilator 12 at the set position, a conventional guide wire is inserted through the lumen 20 and advanced into the disc at the target site so as to provide an anchoring effect for the assembly 10. Thereafter, the second dilator 32 and subsequent dilators, are introduced and neural monitoring is conducted in the same manner as described above.

Figure 12:
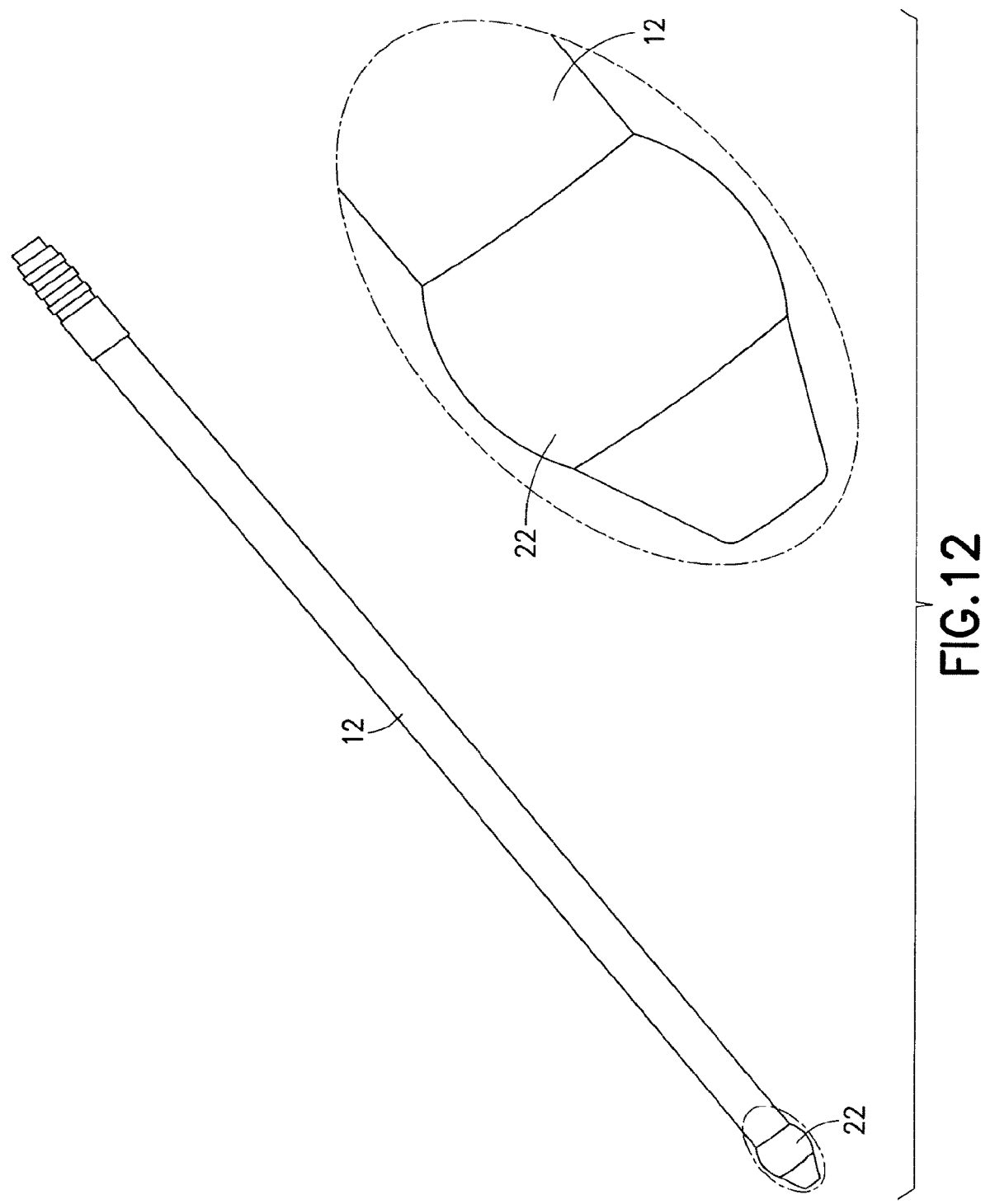
FIG. 12 depicts a bulbous electrode useable in accordance with the subject invention.
Figure 13:
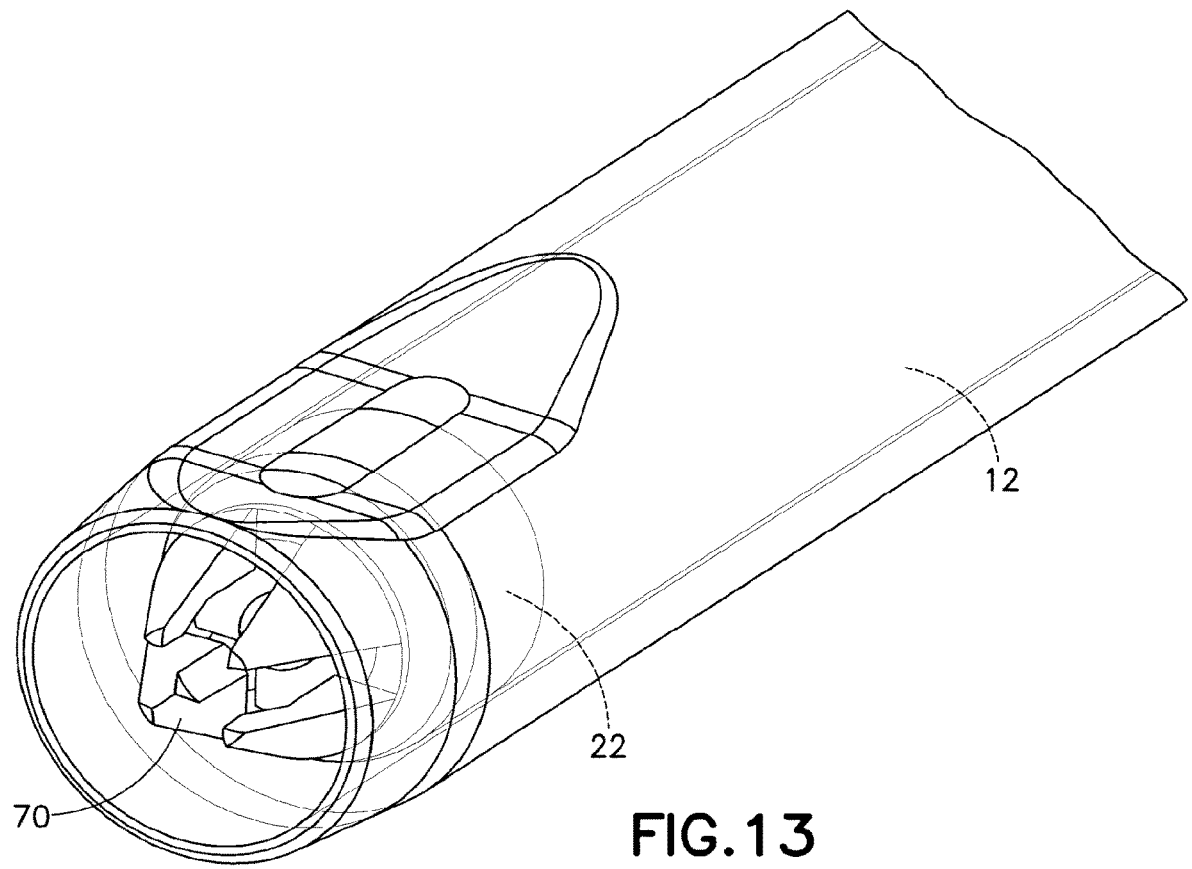
FIG. 13 depicts a plastic clip useable with the subject invention.

As will be appreciated by those skilled in the art, the electrode 22 may be formed of various configurations, such as having a generally cylindrical shape (FIG. 7), with the outer surface being generally flat, or with a bulbous shape, as shown in FIG. 12. The electrode 22 may also have a tapered portion to match the profile of the first dilator 12 (FIG. 2). In addition, the electrode 22 may be attached to the tubular body 14 such as being seated within a slot therein, or may be fixed by a plastic ring 70 mounted at the distal end 16 of the tubular body 14 (FIG. 13).

Figure 14:
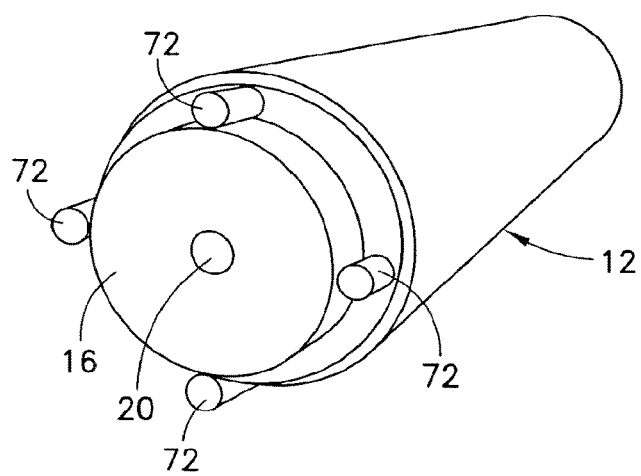
FIGS. 14 and 15 show a variation of the subject invention utilizing a plurality of electrodes with a discrete window formed in the second dilator.
Figure 15:
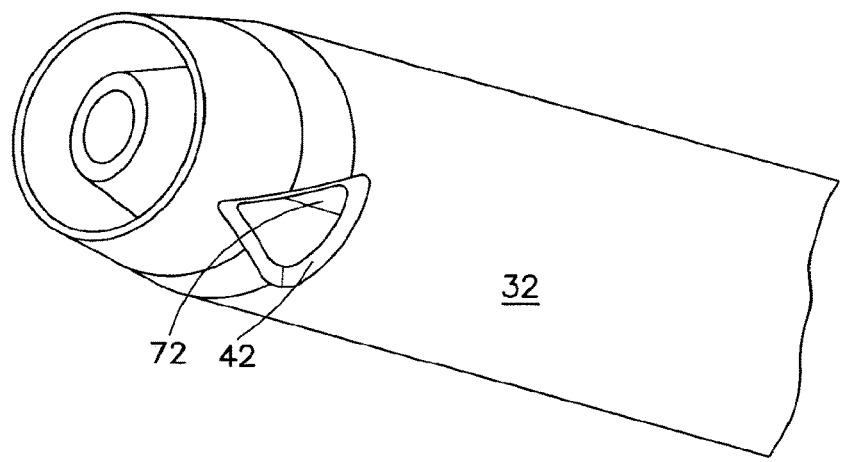

As will also be appreciated by those skilled in the art, the electrode 22 may be replaced by a plurality of electrodes 72 circumferentially spaced, preferably equally, about the first dilator 12 (FIGS. 14 and 15). Preferably, four equally-spaced electrodes 72 are utilized. This version may be used in the same fashion as described above with respect to the electrode 22, with the electrodes 72 in this version being all simultaneously coupled to the source of electricity 48. The window 42 is caused to be rotated about the electrodes 72 in the same fashion as described above.

Figure 16:
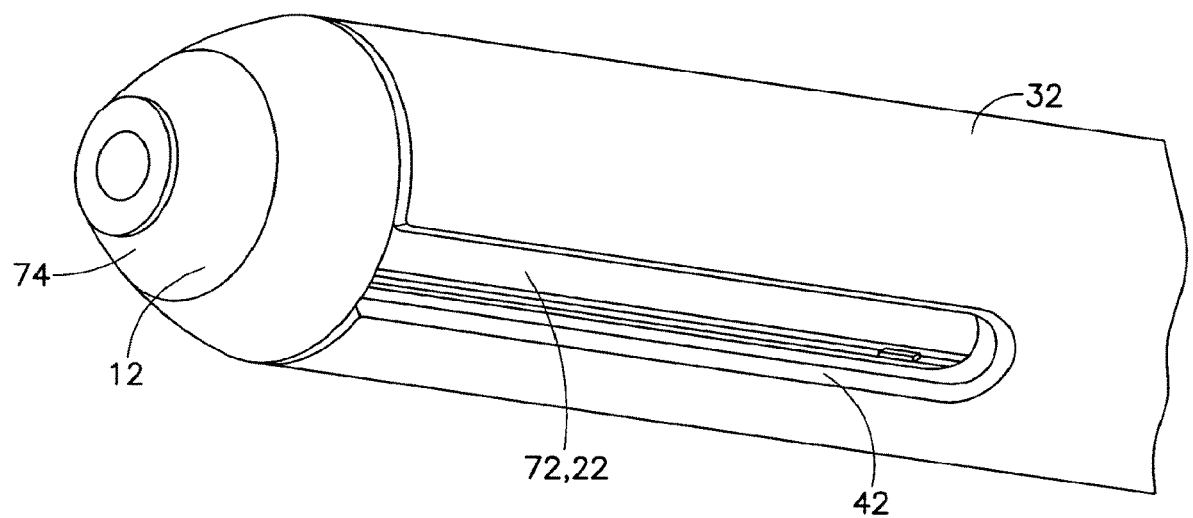
FIG. 16 shows a variation of the subject invention with the first and second dilators being pre-assembled for use.

With reference to FIG. 16, the first and second dilators 12, 32 may be assembled pre-insertion for collective insertion into the body. Here, the first dilator 12 may include blunt-nosed tip 74 to act as a leading end for insertion.

With the use of the plurality of electrodes 72, the electrodes 72 may be configured to be separately electrified in turn about the circumference of the first dilator 12. Here, the first dilator 12 is useable in conjunction with the second dilator 32 in the same manner as described above, except that a window 76 is provided for each of the electrodes 72 (FIG. 17). During use, with the second dilator 32 being located about the first dilator 12, the windows 76 are all in simultaneous registration with corresponding electrodes 72 so as to simultaneously expose all of the electrodes 72. Current is then caused to be sequentially introduced into each of the electrodes 72 in turn. Electrical activity is monitored to determine which, if any of the electrodes 72, develops a "hit" (electrical activity in one of the muscle electrodes). The direction of the nerve is determined based on the related electrode 72 which is electrified and the muscle in which activity was noted. No adjustment (i.e., rotation) of the second dilator 32 is necessary relative to the first dilator 12 for this variation.

As a further variation, the second dilator 32 may be formed completely solid, with no windows therein (FIG. 18). With this arrangement, the electrodes 72 may be formed to be distally exposed in the first dilator 12, such as shown in FIG. 18. This may be achieved by extending the electrodes 72 into the portion 37 or the blunt-nosed tip 74 so as to extend therefrom. Recesses 78 may be formed in the portion 37 or the blunt-nosed tip 74 in which the electrodes 72 may be seated and exposed without the electrodes 72 having to extend outwardly therefrom.

In an alternative arrangement as shown in FIGS. 19-21, a first dilator 112 may be provided with the tubular body 114 being of electrically-insulative material having the channels 66 formed about a circumference thereof in the same manner as described with respect to the third dilator 56 shown in FIGS. 8 and 8A. With this arrangement, the first dilator 112 does not include any electrodes, and the second dilator 32 may be completely eliminated. The first dilator 112 may be introduced to the target site with or without the use of the monopolar probe 46 as described hereinabove. With the first dilator held in position, a monopolar probe 46 may be sequentially inserted into the channels 66 of the first dilator 112 in the same manner as described above with respect to the third dilator 56 to evaluate proximity of nerves in each of the four quadrants. Thereafter, a third dilator 56 or fourth dilator 68 may be used as described above as desired by the surgeon.

What is claimed is:

1. A system for monitoring neural activity in bodily tissue and for dilating the monitored tissue, said system comprising:
   a first dilator having a first tubular body of electrically-insulative material, said tubular body having a distal end, a proximal end, and a plurality of axially extending generally straight open channels formed through said first tubular body about a circumference thereof and extending from said proximal end towards said distal end, said first tubular body further having at least one transverse channel in communication with a distal terminus of at least one said axially extending channel and through said tubular body, said at least one transverse channel having a circumferential expanse greater than a circumferential extent of said at least one axially extending channel, said circumferential expanse extending only transversally from the at least one axially extending channel and extending only a limited extent so as to not circumscribe said tubular body; and,
   a probe formed to be sequentially introduced into each of said axially extending channels, said at least one transverse channel providing for enhanced signal transmission from said probe when disposed in said at least one axially extending channel and in axial alignment with said at least one transverse channel.

2. A system as in claim 1, wherein said tubular body has a plurality of said transverse channels, each one of said plurality of transverse channels being in communication with a distal terminus of each respective one of said axially extending channels.

3. A system as in claim 1, wherein said axially extending channels are disposed at four substantially equally spaced locations about the circumference of said tubular body.

4. A system as in claim 1, further comprising a second dilator having a second tubular body of electrically-insulative material, said second tubular body having a distal end, a proximal end and a lumen extending therebetween sized to permit said second dilator to telescopically slide over said first dilator, a plurality of second axially extending channels being formed about a circumference of said second tubular body of said second dilator, each of said plurality of second axially extending channels being formed to accommodate said probe.

* * * * *